US00PP23602P3

(12) United States Plant Patent
White

(10) Patent No.: US PP23,602 P3
(45) Date of Patent: May 21, 2013

(54) MINIATURE ROSE PLANT NAMED 'SAVABOO'

(50) Latin Name: *Rosa hybrida*
Varietal Denomination: SAVaboo

(75) Inventor: Wendy R. White, Ipswich, MA (US)

(73) Assignee: Greenheart Farms, Inc., Arroyo Grande, CA (US)

( * ) Notice: Subject to any disclaimer, the term of this patent is extended or adjusted under 35 U.S.C. 154(b) by 10 days.

(21) Appl. No.: 13/317,122

(22) Filed: Oct. 11, 2011

(65) Prior Publication Data

US 2013/0091608 P1 Apr. 11, 2013

(51) Int. Cl.
*A01H 5/00* (2006.01)

(52) U.S. Cl.
USPC ..... Plt./116

(58) Field of Classification Search
USPC ..... Plt./116
See application file for complete search history.

*Primary Examiner* — Susan McCormick Ewoldt

(57) ABSTRACT

'SAVaboo' is a new and distinct variety of hardy miniature rose plant, identified by its bi-color blooms of a noticeable bright orange-red offset by the deep yellow at the center and covering the reverse of the petals. The plant is vigorous and a profuse bloomer, making it ideal as a specimen plant, in a border, or in a container.

1 Drawing Sheet

Genus species: *Rosa hybrida.*
Varietal denomination: 'SAVaboo'.

BACKGROUND OF THE INVENTION

This present invention relates to a new and distinct variety of hardy, bush type rose plant of the miniature rose class. This new variety was developed by me under controlled conditions in a greenhouse in Rowley, Mass., by crossing the following rose plants in the spring of 2000:

The seed parent was a seedling I had developed previously by crossing the hybrid tea rose 'TANellis' (U.S. Pat. No. 2,574) as seed parent with an unnamed, unintroduced miniature seedling from this same hybridizing program.

The pollen parent was a miniature rose, 'Baby Katie' (U.S. Pat. No. 4,471).

The idyllic goal of this breeding program was to produce unique abundantly and continuously flowering miniature roses with exhibition, hybrid tea form flowers, and preferably with the qualities of fragrance, disease resistance and hardiness. Both parent roses chosen for this cross displayed abundant, hybrid tea form bloom production with some degree of fragrance and above average disease resistance. Additionally, the pollen parent had proven itself quite hardy. (The seed parent was not tested for this.)

I harvested and planted 345 seeds from this cross, with 104 seedlings germinating. Eight of those seedlings were selected to watch further. The current plant is the only seedling to be tested and introduced; all but one of the remaining seedlings have been destroyed with that one, along with the current plant, being used in future hybridizing. The current plant is a miniature rose plant with abundant production of hybrid tea form, mildly fragrant flowers, good resistance to diseases and insects, and proven hardiness.

This current plant may be compared with its parents, as shown here in Table 1.

TABLE 1

| | Seed parent: seedling | Current plant: 'SAVaboo' | Pollen parent: 'Baby Katie' |
|---|---|---|---|
| BLOOM COLOR | Salmon-Orange | Orange-Red and Deep Yellow Bicolor | Salmon-Pink and Light Yellow blend |
| BLOOM SIZE, FULLY EXPANDED | average: 2½ inches | average: 1¾ to 2 inches | average: 1½ to 1¾ inches |
| PLANT SIZE | 2½ feet tall and wide | 10 to 16 inches tall 10 to 14 inches wide | 12 to 16 inches tall; 10 to 12 inches wide |
| FOLIAGE | matte | semi-glossy | semi-glossy |

Asexual reproductions by cuttings of this new rose cultivar in Rowley, Mass. and Arroyo Grande, Calif. has shown all distinguishing characteristics continually come true to form.

SUMMARY OF THE INVENTION

The present invention relates to a new and distinct cultivar of hardy, dwarf, bush type rose plant of the miniature class. The features distinguishing it from its parents and from all other varieties of which I am aware are its unique combination of the following:

- a bright orange-red flower color set off by the deep yellow color at the base of and on the reverse of its petals;
- the length of time these flowers hold their bright coloring;
- the hybrid tea type form of its flowers;
- the mild to moderate, sweet fragrance of the flowers;
- its near continuous flowering habit;
- its petal count;
- a plant with uniformly well-branched and slightly spreading habit;
- its medium green, semi-glossy foliage;
- its good resistance to rose diseases;
- its ability to root easily from cuttings.

The flowers only of the current plant are compared to those of other bi-colored roses from this same hybridizing program here in Table 2.

TABLE 2

| ROSE PLANT | COLOR FIRST FEW DAYS | PETAL COUNT | BLOOM SIZE |
|---|---|---|---|
| Current Plant: 'SAVaboo' | Bright orange-red upper surface, darkest along edges, deep yellow center and reverse | 17 to 27 | 1⅝ to 2⅜ inches |
| Unnamed sister seedling of current plant | Light apricot-orange upper surface with very light apricot-yellow center and reverse | 26 to 30 | 1½ to 134 inches |
| 'SAVachase' U.S. Plant Pat. No. 7,058 expired | Medium yellow petals have red margins that become more prominent as light intensifies | average: 21 | 1⅛ to 1¼ inches |
| 'SAVabusy' App. Ser. No. 20030115643, abandoned | Orange upper surface, yellow reverse and center of petals | 35 to 40 | 1¼ inches |
| 'SAValights' U.S. Plant Pat. No. 8,918, expired | Medium yellow petals edged with medium red | 30 to 35 | 1½ inches |

Table 3 compares only the plant habit of the current plant to that of those same roses from this hybridizing program. The unnamed, unintroduced sister plant from this same cross has the same plant habit as the current plant, 'SAVaboo'.

TABLE 3

| Rose Plant | Plant Habit | Plant height | Foliage |
|---|---|---|---|
| Current Plant: 'SAVaboo', and its sister seedling | Bushy; well branched | 10 to 16 inches | Medium-green, semi-glossy |
| 'SAVachase' | Compact; well branched | 10 to 15 inches | Semi-glossy; deep bluish-green color |
| 'SAVabusy' | Bushy; spreading to 2 feet | 14 to 22 inches | Matte; very dark, deep green color |
| 'SAValights' | Upright; well branched | 16 to 20 inches | Semi-glossy; deep green color |

BRIEF DESCRIPTION OF THE DRAWING

The accompanying color image is compiled of four separate images.

The largest image taken in mid August, #1, is of 'SAVaboo' as grown in 5-inch pots, outdoors in Ipswich, Mass. All different stages of growth plus bud and flower development are displayed.

Images #2 and #3 show specimens of opening buds and flowers of 'SAVaboo' from plants grown in 10-inch nursery containers in a greenhouse in Arroyo Grande, Calif. Various features of the stems are clearly visible in these images.

Image #4 is a closer view of the opening flowers, also taken from plants grown in a greenhouse in CA except from plants growing in 6-inch pots and earlier in the season.

Colors are depicted as nearly correct as is possible to make in a color illustration of this character.

BOTANICAL DESCRIPTION OF THE PLANT

The following observations, measurements, values and comparisons describe 1 to 2 year old plants of *Rosa hybrida* 'SAVaboo', of the miniature rose class. These plants began their life in a greenhouse in Arroyo Grande, CALIF. At 9 to 12 months of age, they were shipped to Ipswich, Mass. where they were grown under lights for 8 months, and finally moved outside in early June where they were observed for an additional 12 weeks. Significant differences were noticed between each location showing the phenotypic expression varies with environmental, cultural and climatic conditions. Colors were lighter and less intense and flower and foliage sizes were larger in locations of lower light intensity. Descriptions used here are observations of the plants after they were outside in Ipswich, Mass., unless otherwise noted. The information is presented here in outline form. Color references are made using The Royal Horticultural Society (London, England) Colour Chart except where common terms of color are used.

FLOWERS

Blooming habit: Fast repeat to near continuous.

Borne: Mostly singly and occasionally in tight sprays of 2 to 4.

Bud:

*Size*.—About ⅜ inch diameter; about ½ inch long.

*Form*.—Ovate with an acute tip and truncated at the base.

Color when sepals first divide: A deep Buttercup Yellow, near 15B, with a Tangerine Orange, near 24C, along the petal edges.

Bloom:

*Form*.—The bloom starts with a flattened upper profile; both the upper and lower profile became flattened convex, with the upper profile appearing jagged because of the degree of quilling of the petals as the flowers matured.

*Size*.—When fully expanded, the diameter is 1 23/32 to 2⅜ inches, with a depth of 20/32 to 1 16/32 inches. Diameter was directly related to depth.

*Lasting quality on plant*.—In cool temperatures of 60° to 65° F., petals remained fresh up to 11 days before colors started to fade, with a total of 16 to 20 days before petals began to drop.

*Fragrance*.—Mild to moderate, sweet.

*Petalage*.—17 to 27.

*Petaloids*.—None to 8; quantity of petaloids is not relative to the quantity of the petals.

Petals:

*Texture*.—Adaxial surface was velvety but somewhat rugose; abaxial surface was more rugose and a bit satiny.

*Appearance*.—The adaxial surface had all veins slightly recessed, and of a somewhat lighter color than the surrounding petal surface. The abaxial surface also showed the veins recessed but with no notable difference in their color.

*Form*.—Outer petals were broad spatulate with an acute apex that was minutely notched on either side of the tip. Intermediate and inner petals were obovate; the apex was more distinct and the notches on either side were gone or barely noticeable.

*Margins*.—Of the outermost petals were nearly flat; margins of the remaining outer petals were obtuse.

*Size outer petals*.—On the full open bloom, widths varied from 25/32 to 31/32 inch and lengths varied from 28/32 to 29/32 inch.

*Arrangement*.—Imbricated.

*Persistence*.—Remained attached to receptacle until well after fade, 16 to 20 days.

*Color*.—During the first few days the adaxial surface was a scarlet red between 46B and 46C. The basal area was a Lemon Yellow, near 13B. The point of attachment was a deep Buttercup Yellow, near 15A. The abaxial surface was a Guardsman Red near 45A along the margins and blended into the Primrose Yellow, near 4B, from the basal area. It sometimes appeared near 24B, a Tangerine Orange, in places where the red from the adaxial surface showed through the Primrose Yellow. The point of attachment was also near 4B. The adaxial surface of the inner petals was a bit lighter, between 46C and 47B. The basal areas and points of attachment of the intermediate petals were the same as the outer petals, and of those of the inner petals were near 5B. The abaxial surface also appeared lighter, near 24C. Progressing inward toward the center of the flower, the basal area became more near 5C, a Dresden Yellow, and a bit darker, near 5B, on the innermost petals. Points of attachment were near 2B, but near 5B on the innermost petals. When full open, the adaxial surfaces of all petals had lightened somewhat to near 43B, a Scarlet Red, with a few streaks and flecks in the outer petals of a Buttercup Yellow, between 16C and 16D. Basal areas had become a bright yellow, between 9A and 12A. The points of attachment were near 12A. The abaxial surface appeared near 25C, a Nasturtium Orange. The basal area was near 12A and the point of attachment was near 14B.

*Color as the blooms continued to age.*—Yellow tones faded gradually away and adaxial surfaces, most clearly visible, faded to a Claret Rose near 50B, then to a Neyron Rose near 55B and finally to a Rose Bengal near 57C before the petals began to drop.

Petaloids:

*Texture and color.*—The same as the inner petals.

*Size.*—Widths varied from 4/32 inch to 23/32 inch; lengths varied from 7/32 inch to 1 5/32 inches, not relative to width.

*Unique characteristics.*—The main vein was distinct, always marked by a yellow streak between 12B and 5C, and was at or near the center of the petaloid or along one edge. Form was bifid or cleft at the main vein; distorted, as the lower portion of a petal with a ragged margin; and/or attached by a filament. When the main vein was along one edge there sometimes was an entire or part of a sterile stamen attached. Any or all of these and other shapes appeared within each flower at the same time.

General tonality: Bright orange-red and deep yellow bicolor.

Sepals: Extended beyond the tip of the bud by 8/32 to 12/32 inch. They were permanently attached to the receptacle, rolled back just ahead of the petals, curling back to eventually wrap completely up around the receptacle, and remained thus as the hip matured.

*Size.*—Lengths varied from 17/32 to 21/32 inch on each flower; widths were most often 7/32 inch varying between 6/32 and 8/32 inch, not relative to length.

*Color.*—Near 144C at the base and center of the outer surfaces, gradually became darker, between 146B and 147B, progressing toward the apex. Apices were a very dark yellow-green, between 146A and 147A. Anthocyanin coloring was sometimes present, seemingly most often in the cooler temperatures and absent in warmer temperatures. It may be strong on the sunward side of the bud near 181A, a medium color from the Greyed-Red Group, or more often near 176A, a darker color from the Greyed-Orange Group. Some areas of the sepal surfaces were flushed heavily, some lightly flushed and some not at all. Inside surfaces appeared light grayed-green because of the fine pubescent covering, with the centers appearing between 194A and 145C, and along the margins appearing near 191A. Apices were a very dark yellow-green, near 147A, and without any pubescent covering.

*Form.*—Ovate and truncated at the base. Outermost sepals had lanceolate apices and inner sepals had attenuate apices.

*Surface texture and appearance.*—Surfaces appear matte. The surface of the outermost sepals had some randomly located fine hairs and stipitate glands. As they aged, the stipitate glands increased in quantity and developed into near evenly spaced, horizontal, near parallel rows. The innermost sepals had more hairs covering the surface and a few seemingly, randomly located stipitate glands that increased in quantity as they aged, particularly in the basal area.

*Margins.*—Outermost sepals had stipitate glands and hairs along the margins; the hairs increased in quantity as they aged. Along each margin were 1 to 3 foliar appendages; most were broadly serrated with a gland at the tip of each serrate. Innermost sepals were lined only with hairs and no foliar appendages.

Peduncle: Remained firmly attached to the stem until well after it had dried up.

*Aspect.*—Erect, often with a slight curve sunward.

*Size.*—Lengths varied from 23/32 inch to 1 6/32 inches, with the longest peduncles attached to the longest stems.

*Color.*—A Lettuce Green, near 144A.

*Texture.*—Glossy to semi-glossy.

*Surface.*—Glands and stipitate glands.

Receptacle: Urceolate.

*Size.*—Diameter was uniformly around 7/32 inch; height varied from 7/32 to 10/32 inch up to and including when the sepals began to divide.

*Color.*—Noted to be near 144A; or lighter, between 143C and 144B; or even lighter, near 143C, on the same plant on the same day.

*Texture/appearance.*—Glabrous/semi-glossy.

REPRODUCTIVE ORGANS

Stamens, filaments and anthers:

*Arrangement.*—Regularly arranged around styles, often in a double row tightly adjacent to the petaloids.

*Quantity.*—Counted 65 to 93.

*Filaments.*—Length varied from 5/32 to 8/32 inch within each flower with the longer lengths in the outermost row, furthest from the pistils.

*Color.*—A Cadmium Orange, near 23B.

*Anthers.*—Color of a Chrome Yellow, near 14D.

*Pollen sacs.*—Color of a Saffron Yellow, near 21A.

Pistils, styles, and stigmas.—Originated in an alveola in the center of the top of the receptacle.

*Quantity.*—About 1/3 to 1/2 the number of stamens, counted 24 to 31.

*Styles.*—Thin; the longer ones were sometimes slightly curled.

*Length.*—5/32 to 11/32 inch, varied by 3/32 or 4/32 inch in each flower.

*Color*.—Near 46D, Delft Rose, immediately below the stigma, and a Naples Yellow, near 11B, as they proceeded into the alveola.

*Stigmas*.—A dull yellow, between 11C and 162C.

Hips: Only a relative few were observed to full maturity.

*Shape*.—Globoid.

*Size*.—Diameters were measured from 20/32 to 22/32 inch by 23/32 to 25/32 inch; heights were measured from 19/32 to 23/32 inch and also often varied by up to 3/32 inch from one side of the hip to the other.

*Surface texture*.—Glabrous.

*Color when mature*.—The color when grown under lights varied from deep orange, between 169B and 169C to a Nasturtium Orange near 25B on the side with most direct exposure to the lights. With less exposure the color was less intense and less orange, near 163C from the Greyed-Yellow Group. The side away from direct light was a medium green, between 143C and 144A.

Seeds: Did not protrude from the top.

*Seed color*.—From hips on the plants grown under lights, a very pale beige, between 159D and 159C, from the Orange-White Group.

*Seed shape*.—Somewhat oblate, but not smooth or uniform.

*Seed size*.—From these same hips, diameters varied between 5/32 to 6/32 inch by 7/32 to 8/32 inch and lengths of 8/32 to 11/32 inch.

PLANT

Habit: Upright, well branched, compact.

Growth: Very vigorous.

*Size*.—10 to 16 inches tall and 10 to 14 inches wide.

*Root initiation from cuttings*.—Under controlled greenhouse conditions, 3 to 5 days.

*Length of flowering stems*.—Variable, depending on the distance from the point of origination to the crown of the plant. Flowering stems originated from other flowering stems, sometime after the sepals divided, and were usually one or two inches shorter than the stems from which they originated. Lengths of flowering stems were measured from 3 24/32 to 4 24/32 inches; flowering stems originating from those stems were measured 2 24/32 to 3 22/32 inches long; stems originating from those stems were measured around 1 22/32 inches long.

Foliage: Pinnately compound, most often with 5 leaflets but also with 3, 6 or 7. Three-leaflet leaves were usually located as the last leaf before the connection to the peduncle. Six and seven-leaflet leaves were usually located at or near the base of the flowering stems.

*Size of mature leaf*.—(Measurements of the foliage are from the plants when there were growing under lights.) Six- and seven-leaflet leaves were shorter than other leaves, most likely because of their location at the base of the flowering stems. Lengths of five-leaflet leaves varied from 3½ to 4 inches; lengths of 7 leaflet leaves varied from 2½ to 2⅞ inches.

*Leaflets*.—Narrow-ovate, often with a stipel at one or both sides of the base.

*Size of terminal leaflet*.—On five-leaflet leaves lengths varied from 1 9/16 to 1 12/16 inches. On seven-leaflet leaves the lengths were shorter, from 31/32 inch to 1 3/16 inches. Widths on five-leaflets leaves varied from 13/16 to 1 inch; on seven-leaflet leaves they varied from 9/16 to 14/16 inch.

*Color new foliage*.—(Colors of the foliage were very near the same whether the plants were growing under lights or in direct sun.) The adaxial surface started a dark green near 139B but, after a day or two, became darker, near 139A; this was flushed in varying degrees with a dark red, between 185A and 187A, being most intense on the newly opening foliage. The abaxial surface was lighter, near 191A, flushed in varying degrees with Chrysanthemum Crimson, near 185A, on newly opening leaves, and a darker color, near 187A, as they expanded.

*Color older foliage*.—Anthocyanin color was absent. The adaxial surface was still near 139A; the abaxial surface was darker than on the young foliage, between 191A and 189A.

*Appearance*.—The main vein on the adaxial surface was completely recessed, with the other veins being somewhat recessed. All veins protruded on the abaxial surface.

*Texture*.—Adaxial surface was semi-glossy with some long hairs randomly scattered around the surface. The abaxial surface was matte and somewhat leathery, with a few long hairs, sometimes in a cluster, and none to a few stipitate glands along the main vein.

*Edge*.—Serration was very fine and usually simple, with two or more serrates sometimes doubled but along only one margin. Each serrate was tipped with a gland. Randomly, a stipitate gland appeared between some serrates.

*Petiole*.—Color on the adaxial surface on young foliage was between 187B and 183A along the ridge and near the same or somewhat lighter, between 187C and 183D, in the groove. The abaxial surface was near 187D. On older foliage, the color on the ridges on the adaxial surface was the same as the adjacent leaf surface; the color in the groove was lighter, between 137D and 146C. The abaxial surface was between 138B and 145B.

*Size*.—On five-leaflet leaves the length varied from 20/32 inch to 1 2/32 inches; on seven-leaflet leaves length varied from 21/32 to 26/32 inch.

*Texture/appearance*.—Along the ridge of the adaxial surface were numerous short upright hairs and a few stipitate glands; the groove had a light covering of these same hairs with a greater concentration just below the juncture with the rachis. The abaxial surface had some short hairs and some stipitate glands, all randomly located.

*Rachis*.—Color of the rachis was the same as that of the petiole. Size: On five-leaflet leaves lengths varied from 20/32 to 28/32 inch. On seven-leaflet leaves lengths varied from 14/32 inch to 1 1/32 inches. Texture/Appearance: The adaxial surface had a few more stipitate glands along the ridges than were found on the petiole, but the same short, upright hairs were along the ridges and in the groove. A larger quantity of these hairs was located just above and below the junctures of the petiolules. None to two prickles were found on the abaxial surface, relative to the age and length of the rachis, but there were several stipitate glands regardless of age or length.

*Petiolules*.—Color was the same as that of the petiole and rachis, with the exception that the anthocyanin coloring took longer to fade. Size: length to terminal leaflets varied from 16/32 to 19/32 inch on five-leaflet leaves and from 8/32 to 12/32 inch on seven-leaflet leaves. Texture/Appearance: Petiolules to the terminal leaflets had some stipitate glands and a few hairs along the ridges and only a few hairs in the groove, except for a cluster of hairs at the base of the juncture with the leaflet. On the petiolules to the other leaflets, one or two stipitate glands and a few long hairs were found only along the ridge closest to the base of the leaf. There were none to a few long hairs in the groove. On the abaxial surfaces of the petiolules to the terminal leaflets were a few stipitate glands and a few hairs, with a cluster of long hairs at the juncture with the leaflet. Abaxial surfaces of petiolules to the other leaflets were near glabrous, occasionally having a few hairs.

*Stipules*.—Paired at the base of each petiole and quite variable. Size: size was relative to the length of the petiole to which they were attached. Lengths ranged from 6/32 to 16/32 inch attached and 4/32 to 8/32 inch angled outward at anywhere from 30° to 90° from the petiole. Lengths within each pair varied by 1/32 to 3/32 inch. Lengths angled outward were relative to the length of that part of the stipule attached to the petiole. Margins: Sparsely and unevenly serrated, with a gland at the tip of each serrate, and with glands and stipitate glands randomly located between serrates. Margins of the tips angled outward had no hairs and only a few stipitate glands. Edges: curled back slightly around mid length only.

Other foliar appendages: At the point where the stem connected with the peduncle there were one or more simple leaves with stipules attached the length of the petiole, and/or connate stipulate appendages.

Resistance: Above average resistance to blackspot and moderate resistance to powdery mildew were observed. Downey mildew and rust were not observed.

Wood:

*Color new wood*.—A Scheele's Green, near 144B.

*Color old wood*.—A darker yellow-green, near 146A.

*Texture new wood*.—Somewhat glabrous; some glands were present.

*Texture old wood*.—Lenticels formed in the third or fourth year of growth, starting at the base of the oldest canes, in parallel, vertical rows. The color of the lenticels was a medium brown near 165A, from the Greyed-Orange Group.

*Cane diameters*.—About 12/32 inch at the base of the main canes; 7/32 to 8/32 inch at the base of the primary laterals; from 3/32 to 5/32 inch, most often 4/32 inch, at the base of flowering stems, and was not relative to the length of the stem.

Prickles:

*Quantity*.—1 or 2 between each node. Flowering stems on the plants growing in MA had no prickles; the accompanying patent image shows they are present on the plants grown in the greenhouse in CA.

*Length*.—Between 7/32 and 8/32 inch, most often 7/32 inch.

*Form*.—Angled and gently curved downward, on a near oblong-shaped base.

*Color*.—When young, the color of the prickles seemed to vary randomly within the Greyed-Yellow Group: some were between 162D and 160C; some were between 160B and 162B; some were darker, from the Greyed-Orange Group, near 165B. When old, the prickles were a dark brown, near 165A.

Hardiness: This current plant, *Rosa hybrida* 'SAVaboo', has been tested hardy to Zone 5.

I claim:

1. A new and distinct variety of hardy, miniature rose plant, substantially as illustrated and described, having flowers of a vibrant orange-red with a deep yellow center and reverse, on a vigorous, upright growing plant, having a somewhat spreading habit, and dark green, semi-glossy foliage, suitable for production from softwood cuttings.

* * * * *

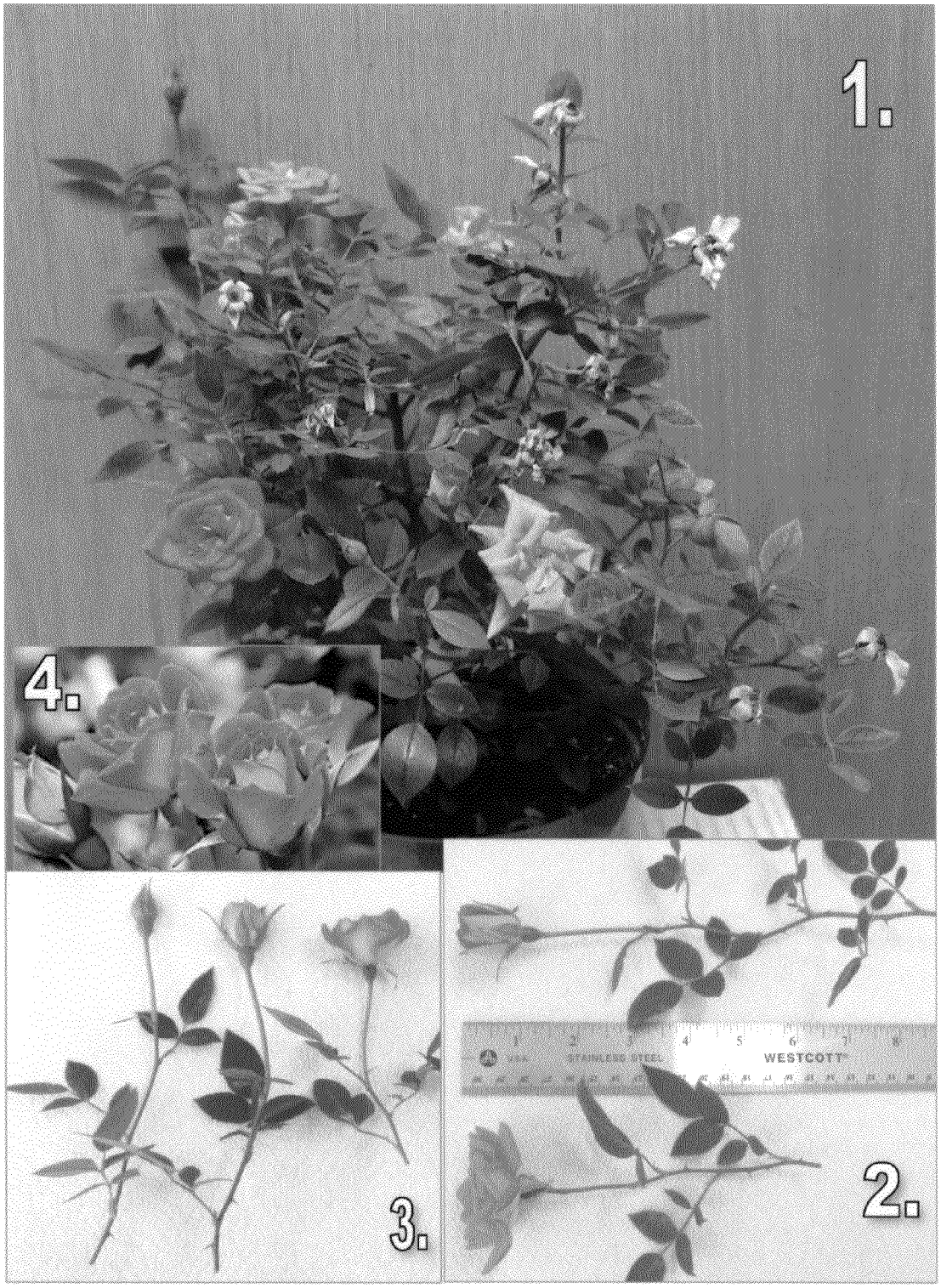
1.
4.
3.
2.
WESTCOTT